US00PP29614P3

(12) United States Plant Patent
Van Swieten

(10) Patent No.: US PP29,614 P3
(45) Date of Patent: Aug. 21, 2018

(54) ***PHALAENOPSIS* ORCHID PLANT NAMED 'PHALFMACON'**

(50) Latin Name: ***Phalaenopsis* hybrid**
Varietal Denomination: PHALFMACON

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 30 days.

(21) Appl. No.: 15/330,841

(22) Filed: Nov. 8, 2016

(65) Prior Publication Data

US 2018/0132407 P1 May 10, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Keith O Robinson
(74) *Attorney, Agent, or Firm* — Jondle & Associates, P.C.

(57) ABSTRACT

A new and distinct variety of *Phalaenopsis* plant named 'PHALFMACON', particularly characterized by having large white flowers, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFMACON'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFMACON'.

The new *Phalaenopsis* plant is a product of a planned breeding program conducted by the inventor in Bleiswijk, The Netherlands. The objective of this breeding program was to create a new *Phalaenopsis* plant with large white flowers, suitable for potted plant production.

The new *Phalaenopsis* plant 'PHALFMACON' is a result of cross-pollination made by the inventor in August 2006 in Bleiswijk, The Netherlands of the proprietary female, or seed parent, *Phalaenopsis* hybrid '06541-01' (unpatented) with the proprietary male, or pollen parent, *Phalaenopsis* hybrid '23313-02' (unpatented).

The new *Phalaenopsis* was selected by the inventor as a single plant within the progeny of the stated cross-pollination in a controlled greenhouse in Bleiswijk, The Netherlands in August 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALFMACON' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFMACON' as a new and distinct variety of *Phalaenopsis* plant.

1) Large white flowers;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in August 2016. Colors in the photographs may differ from the color values cited in the detailed botanical description, which accurately describe the actual colors of the new variety.

DESCRIPTION OF THE NEW VARIETY

Figure 1:
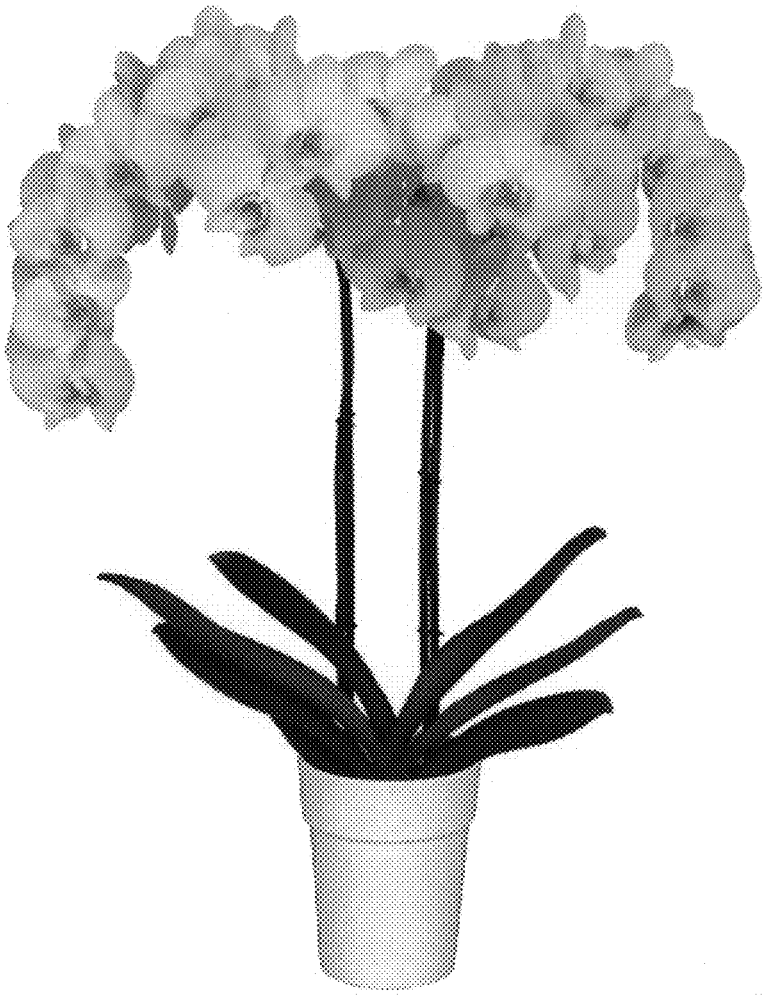
FIG. 1 shows the overall plant habit, including blooms and foliage of 'PHALFMACON'.
Figure 2:
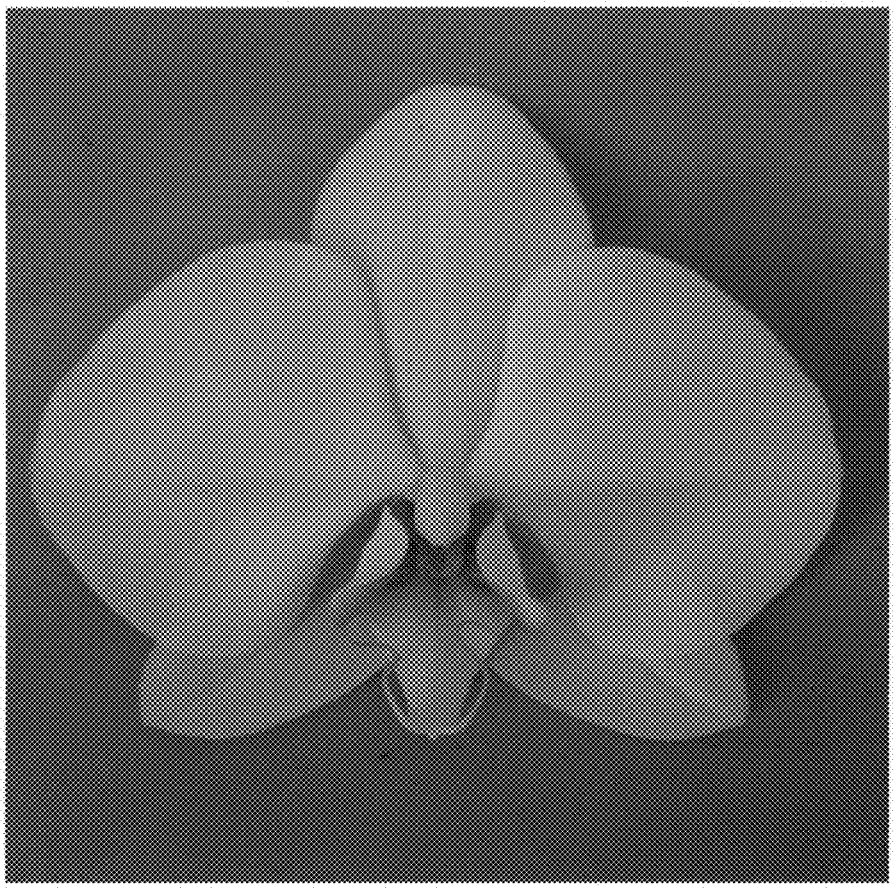
FIG. 2 shows a close-up of a flower of 'PHALFMACON'.
Figure 3:
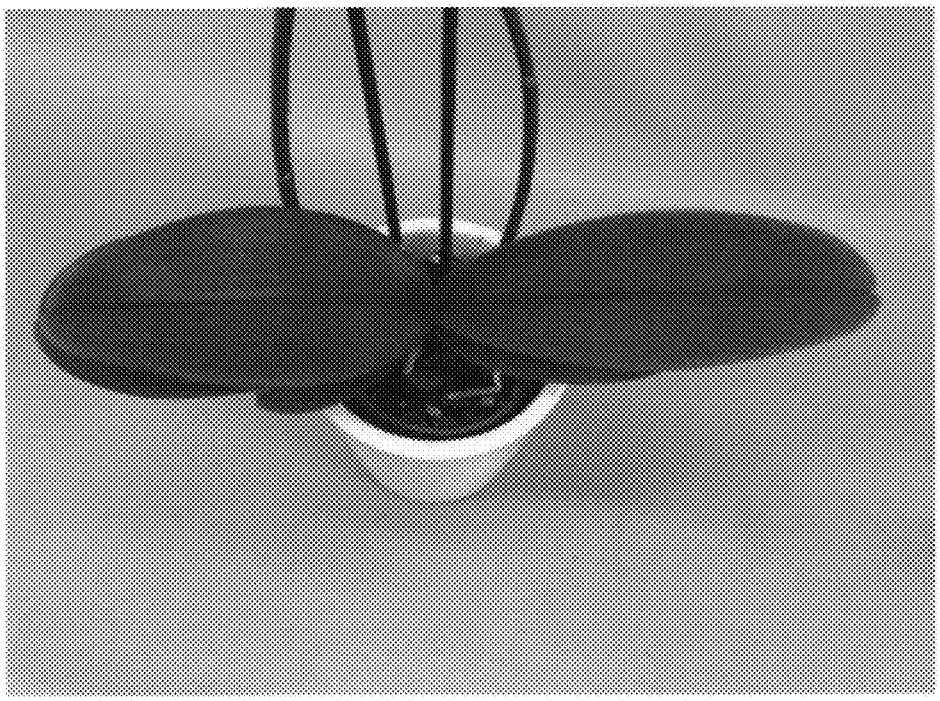
FIG. 3 shows a close-up of the leaves of 'PHALFMACON'.

The following detailed description sets forth the distinctive characteristics of 'PHALFMACON'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in August 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFMACON'.

Parentage:

*Female parent*.—*Phalaenopsis* cultivar '06541-01' (unpatented).

*Male parent*.—*Phalaenopsis* cultivar '23313-02' (unpatented).

Propagation:

*Type*.—Meristem tissue culture.

Roots:

*Root description*.—Greyed-green (RHS 191C/D) colored roots with branching lateral roots having dark red (RHS 187A/B) colored root tips.

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 49.0 cm to 59.0 cm.

*Width* (*measured from leaf tips*).—About 33.0 cm to 38.0 cm.

*Vigor*.—Strong.

Leaves:

*Mature leaves*.—Quantity per plant: 6 to 8 leaves are produced before flowering. Length (fully expanded): 18.0 cm to 20.0 cm. Width: 7.0 cm to 8.0 cm. Shape: Oblong. Base shape: Moderately elongated. Apex: Unequal obtuse. Leaf blade angle with the petiole (measured from the horizontal position): Between 25 degrees and 40 degrees. Leaf margin: Entire. Color: Upper surface: RHS 146A. Lower surface: RHS 146B. Variegation: Absent. Texture: Rough. Thickness: 2.1 mm to 2.4 mm. Venation: Pattern: Parallel. Color of the midvein: Upper surface: RHS 147A. Lower surface: RHS 147B.

Peduncle:

*Quantity per plant*.—1 to 2.

*Number of flowers per peduncle*.—10 to 15.

*Length*.—60.0 cm to 65.0 cm.

*Diameter*.—5.9 mm to 6.3 mm.

*Strength*.—Strong.

*Aspect*.—Upright to slightly pendant.

*Texture*.—Rough.

*Color*.—Brown (RHS 200B) with a touch of green (RHS 146B).

*Internode length*.—30.0 mm to 40.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 220.0 mm to 250.0 mm.

*Number of inflorescences per plant*.—1 to 2.

*Flowering time*.—First flowers can be expected 10 to 11 months after planting in a 12 cm (diameter) pot.

*Flower*.—Height: 90.0 mm to 95.0 mm. Diameter: 105.0 mm to 110.0 mm. Depth of lip: 23.0 mm to 25.0 mm.

*Flower longevity*.—On the plant: 11 to 15 weeks.

*Fragrance*.—Absent.

*Flower bud*.—Average size: Large. Length: 26.0 mm to 28.0 mm. Width: 21.0 mm to 23.0 mm. Shape: Egg shaped. Color: Light green (RHS 145B to 145C) with a touch of diluted purple (RHS N78D).

*Petals*.—Arrangement: Open/free. Shape: Semi-circular. Apex: Rounded asymmetric. Margin: Entire. Length (from base to tip): 50.0 mm to 52.0 mm. Width: 65.0 mm to 67.0 mm. Position of broadest part of petal: At the middle. Color (when fully opened): Upper surface: Basic color: White (RHS NN155C). Over color: Absent Lower surface:. Basic color: White (RHS NN155C). Over color: Absent.

*Dorsal sepal*.—Shape: Broad elliptic. Apex: Rounded to slightly emarginated symmetric. Margin: Entire. Length (from base to tip): 52.0 mm to 54.0 mm. Width: 37.0 mm to 39.0 mm. Color (when fully opened): Upper surface: Basic color: White (RHS NN155C). Over color: Absent. Lower surface: Basic color: White (RHS NN155C). Over color: Diluted light purple (RHS N78D).

*Lateral sepals*.—Shape: Ovate. Apex: Obtuse asymmetric. Margin: Entire. Length (from base to tip): 52.0 mm to 54.0 mm. Width: 28.0 mm to 30.0 mm. Color (when fully opened): Upper surface: Basic color: White (RHS NN155C). Over color: Light green (RHS 145C) at the base. Lower surface: Basic color: White (RHS NN155C). Over color: Diluted light purple (RHS 77D) vein in the middle and light green (RHS 145B) at the base.

*Labellum* (*lip*).—Whiskers: Present. Length of whiskers: 30.0 mm to 32.0 mm. Color of whiskers: Yellow (RHS 13A) and yellow-orange (RHS 17A) towards the tip. Pubescence on the lip: Absent.

*Lateral lobe*.—Shape: Spatulate. Margin: Undulated. Length (from base to tip): 22.0 mm to 24.0 mm. Width: 20.0 mm to 22.0 mm. Color: White (RHS NN155C); yellow (RHS 12A and 15A) on one side towards the edge, with a few stripes (RHS 172B) at the base.

*Apical lobe*.—Shape: Triangular. Margin: Entire. Length: 22.0 mm to 24.0 mm. Width: 23.0 mm to 25.0 mm. Color: White (RHS NN155C); yellow (RHS 7B) and brown (RHS 172C) at the base.

*Callus*.—Average size: Medium. Height: 0.5 cm to 0.7 cm. Length: 0.6 cm to 0.8 cm. Width: 0.4 cm to 0.6 cm. Color: Yellow (RHS 8B and 13A) and dotted (RHS 172B).

*Reproductive organs*.—Column: Length: 9.0 mm to 11.0 mm. Diameter: 6.0 mm to 6.3 mm. Color: White (RHS NN155C). Pollinia: Quantity: 2. Diameter: 1.0 mm to 1.3 mm. Color: Orange (RHS 25B). Ovary:

Length: 9.0 mm to 11.0 mm. Diameter: 2.4 mm to 2.6 mm. Pedicel: Length: 35.0 mm to 37.0 mm. Diameter: 3.0 mm to 3.2 mm. Color: Light green (RHS 145C to 145D) at the base and light purple (RHS 76D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALFMACON' differs from female parent '06541-01' (unpatented) in that 'PHALFMACON' has yellow whiskers with yellow-orange towards the tips and brown peduncles with a touch of green, whereas cultivar '06541-01' has white whiskers with yellow tips and green peduncles with a touch of brown.

'PHALFMACON' differs from male parent '23313-02' (unpatented) in that 'PHALFMACON' has yellow whiskers with yellow-orange towards the tips and brown peduncles with a touch of green, whereas '23313-02' has yellow whiskers and green peduncles with a touch of brown.

'PHALFMACON' is most similar to the commercial *Phalaenopsis* plants named 'PHALCARDOK' (U.S. Plant Pat. No. 25,447) and 'PHALCOXAM' (unpatented). 'PHALFMACON' differs from the commercial variety 'PHALCARDOK' in that 'PHALFMACON' has yellow whiskers with yellow-orange towards the tips, a white lateral sepal lower surface and green (RHS 146A) leaves, whereas 'PHALCARDOK' has yellow-green whiskers, a light green lateral sepal lower surface and green (RHS 137B) leaves. Additionally, 'PHALFMACON' has longer whiskers than 'PHALCARDOK'.

'PHALFMACON' differs from the commercial variety 'PHALCOXAM' in that 'PHALFMACON' has yellow whiskers with yellow-orange towards the tips, whereas 'PHALCOXAM' has white whiskers with yellow tips. Additionally, 'PHALFMACON' has longer whiskers and wider leaves than 'PHALCOXAM'.

I claim:

1. A new and distinct variety of *Phalaenopsis* plant named 'PHALFMACON', substantially as described and illustrated herein.

* * * * *